United States Patent [19]

Aga et al.

[11] Patent Number: 5,863,771
[45] Date of Patent: Jan. 26, 1999

[54] SACCHARIDE COMPOSITION COMPRISING MALTOOLIGOSYLTURANOSE AND MALTOOLIGOSYLPALATINOSE, ITS PREPARATION AND USES

[75] Inventors: Hajime Aga; Takashi Shibuya; Shigeharu Fukuda; Toshio Miyake, all of Okayama, Japan

[73] Assignee: Kabushiki Kaisha Hayashibara Seibutsu Kagaku Kenkyujo, Okayama, Japan

[21] Appl. No.: 810,363

[22] Filed: Mar. 3, 1997

[30] Foreign Application Priority Data

Mar. 4, 1996 [JP] Japan .................................. 8-070915
Mar. 29, 1996 [JP] Japan .................................. 8-099571

[51] Int. Cl.$^6$ .............................. C12P 19/04; C08B 3/06; A61K 31/715; A23G 3/00
[52] U.S. Cl. .............................. 435/101; 435/72; 435/99; 435/100; 536/123.1; 536/124; 536/1.11; 536/4.1; 534/777; 534/54; 534/61; 426/658
[58] Field of Search ................................. 536/123.1, 124, 536/1.11, 4.1; 435/101, 99, 72, 100; 514/777, 54, 61; 426/658

[56] References Cited

U.S. PATENT DOCUMENTS 4,487,198  12/1984  Miyake et al. .
4,521,252   6/1985  Miyake et al. .
5,455,168  10/1995  Maruta et al. .

FOREIGN PATENT DOCUMENTS 0 688 867  12/1995  European Pat. Off. .
57-58905   11/1982  Japan .
58-23799    2/1983  Japan .
58-72598    4/1983  Japan .
05-252974  10/1993  Japan .
07-143876   6/1995  Japan .
08-66188    3/1996  Japan .
2 046 757  11/1980  United Kingdom .

OTHER PUBLICATIONS

Chemical Abstracts, Registry File, Registry #13718–94–0, accessed Dec. 16, 1997.
List of Cultures, Institute for Fermentation, 9th Ed., 1992.
List of Cultures, Institute for Fermentation, 3th Ed., 1962.
Catalogue of Bacteria and Phages, American Type Culture Collection, 18th Ed., 1992.
Fujii, S. et al., "Oligosaccharides Produced by Transglucosidation Action of Protaminobacter rubrum α–Glucosidase.", Seito–Gijutsu–Kenkyukaishi, No. 34, pp. 37–44 (1985).

*Primary Examiner*—Francisco C. Prats
*Attorney, Agent, or Firm*—Browdy and Neimark

[57] ABSTRACT

A saccharide composition comprising maltooligosyl derivatives of turanose and palatinose which can be readily produced, separated, and purified in a relatively-high yield from maltooligosylsucrose by allowing non-reducing saccharide-forming enzymes to act on aqueous solutions containing maltooligosylsucrose. These saccharides are reducing oligosaccharides with a mild and high-quality sweetness and can be used orally and parenterally, as well as being readily metabolized and used by living bodies.

17 Claims, 2 Drawing Sheets

SACCHARIDE COMPOSITION COMPRISING MALTOOLIGOSYLTURANOSE AND MALTOOLIGOSYLPALATINOSE, ITS PREPARATION AND USES

BACKGROUND OF THE INVENTION

1. Field of the Invention

The present invention relates to a saccharide composition comprising maltooligosyl derivative of turanose (hereinafter designated as "maltooligosylturanose") and maltooligosyl derivative of palatinose (hereinafter designated as "maltooligosylpalatinose"), its preparation and uses; more particularly, it relates to a saccharide composition comprising maltooligosylturanose and maltooligosylpalatinose, a process for producing the saccharide composition comprising a step of allowing a non-reducing saccharide-forming enzyme to act on maltooligosylsucrose, and to a composition containing the saccharide composition.

2. Description of the Prior Art

Turanose and palatinose are reducing disaccharides consisting of glucose and fructose moieties and having chemical structures of 3-O-α-D-glucopyranosyl-D-fructose and 6-O-α-D-glucopyranosyl-D-fructose, respectively.

As is disclosed in Japanese Patent Laid-Open No.252, 974/93, it is known that turanose is produced by allowing cyclomaltodextrin glucanotransferase to act on aqueous solutions containing amylaceous substances and fructose. While palatinose is known that, as disclosed in "*Seito-Gijutsu-Kenkyu-Kaishi*", No.34, pp.37–44 (1985), it is produced from sucrose using α-glucosidase from a strain of the species *Protaminobacter rubrum*. These saccharides are known that (i) they have a relatively-low sweetness and less induce dental caries, (ii) they are expected to be used as a material to sweeten food products, (iii) they are readily crystallized, (iv) they could not be readily prepared into high-concentration syrups, and (v) they should be treated or handled in a manner that they may not be crystallized even when used in highly sweetened food products such as bean jams and sweet jellies of beans. The development of non-crystalline oligosaccharides having a higher molecular weight, a satisfactory viscosity-controlling ability, a moisture-controlling ability, and a preferable sweetness, has been greatly expected.

SUMMARY OF THE INVENTION

The present invention provides a process for producing maltooligosylturanose and maltooligosylpalatinose from maltooligosylsucrose in a relatively-high yield and with an easiness on an industrial scale production, a saccharide composition comprising these saccharides produced by the process, and uses thereof.

The present inventors energetically studied methods to produce maltooligosylturanose and maltooligosylpalatinose. As a result, they unexpectedly found that non-reducing saccharide-forming enzymes or maltooligosyltrehalose-forming enzymes, as disclosed in Japanese Patent Laid-Open No.143,876/95 applied by the present inventors, convert maltooligosaccharides into maltooligosyltrehalose and facilitate the production of non-crystalline maltooligosyl-turanose and maltooligosylpalatinose from maltooligosylsu-crose with an easiness and in a satisfactorily high yield, and accomplished the following; (i) a process for producing saccharide compositions comprising these saccharides characterized by allowing the enzyme to act on solutions containing maltooligosylsucrose, (ii) a saccharide composition produced by the process, and (iii) a composition such as food products, cosmetics, or pharmaceuticals containing the saccharide compositions. Thus, the present inventors accomplished this invention.

DETAILED DESCRIPTION OF THE INVENTION

As is disclosed in Japanese Patent Laid-Open No. 143, 876/95, the non-reducing saccharide-forming enzymes usable in the present invention are produced from Rhizobium sp. M-11 (FERM BP-4130), Arthrobacter sp. Q36 (FERM BP-4316), *Brevibacterium helvolum* (ATCC 11822), *Flavobacterium aquatile* (IFO 3772), *Micrococcus roseus* (ATCC 186), *Curtobacterium citreum* (IFO 15231), *Mycobacterium smegmatis* (ATCC 19420), *Terrabacter tumescens* (IFO 12960), and other microorganisms of the genus Sulfolobus as disclosed in Japanese Patent Application No. 166,011/94. These enzymes are intramolecular saccharide-transferring enzymes which convert or rearrange maltooli-gosaccharides into maltooligosyltrehalose. The equilibrium point of these enzymes predominantly inclines to the side of forming maltooligosyltrehalose: For example, they produce maltotriosyltrehalose from maltopentaose as a substrate in a yield of at least about 90 w/w %, on a dry solid basis (the wording "w/w %, on a dry solid basis" as referred to in the present invention will be abbreviated as "%", unless specified otherwise).

In addition to the above enzymes, other enzymes usable in the present invention are those which are derivable from microorganisms of the genera Rhizobium, Arthrobacter, Brevibacterium, Flavobacterium, Micrococcus, Curtobacterium, Mycobacterium, Terrabacter, and Sulfolobus, as well as their mutants capable of producing the desired enzymes and those obtained from transformed microorganisms into which genes coding for the enzymes are introduced, can be selectively used. For example, microorganisms of the genus Sulfolobus such as strains of *Sulfolobus acidocaldarius* (ATCC 33909 and 49426) and *Sulfolobus solfataricus* (ATCC 35091 and 35092) can be advantageously used.

Any synthetic and natural nutrient culture media can be used for culturing the above microorganisms as long as they grow therein and produce the desired enzymes. The carbon sources usable in the present invention include those which can be assimilated by the microorganisms: For example, saccharides such as glucose, fructose, molasses, trehalose, lactose, sucrose, mannitol, sorbitol, and partial starch hydrolysates, and inorganic acids such as citric acid and succinic acid, as well as their salts, can be used. The concentration of these carbon sources is appropriately chosen depending on their types. For example, in the case of using glucose as a carbon source, a preferable concentration is 40 w/v % or lower, more particularly, a concentration of 10 w/v % or lower is more preferably used with respect to the microorganisms' growth and proliferation. The nitrogen sources usable in the present invention are, for example, inorganic nitrogen-containing compounds such as ammonium salts and nitrates, and organic nitrogen-containing compounds such as urea, corn steep liquor, casein, peptone, yeast extract, and meat extract. The inorganic ingredients usable in the present invention are, for example, salts of calcium, magnesium, potassium, sodium, phosphoric acid, manganese, zinc, iron, copper, molybdenum, and cobalt.

Any culture conditions can be used in the present invention as long as the microorganisms can grow and produce the non-reducing saccharide-forming enzymes usable in the invention. Usually, the microorganisms are aerobically cultured at temperatures of about 4°–80° C., preferably, 20°–75° C., and at pHs of 5–9, preferably, 6–8.5. Any culturing time can be used in the present invention as long as the microorganisms can proliferate, preferably, it is about 10–100 hours. Although the concentration of dissolved oxygen (DO) of nutrient culture media is not specifically restricted to, it is usually set to a DO of about 0.5–20 ppm by controlling the aeration rate, stirring rate of nutrient culture media, supplying rate of oxygen to the media, or increasing the inner-pressure of fermentors. The culturing can be carried out batchwise or in a continuous manner.

After completion of the culture, the desired non-reducing saccharide-forming enzymes can be collected from the resulting cultures. Since the activity of the enzymes can be found in both the cells and the cell-free cultures, crude enzymes can be obtained therefrom. Intact cultures can be used as a crude enzyme. Conventional solid-liquid separation methods can be used to separate the nutrient culture media and the cells. For example, centrifugal separation method to directly separate cultures, filtration separation method by precoating or adding filtration agents to the cultures, and separation methods using membrane filters such as plain filters or hollow fibers can be selectively used. Cell-free cultures can be used as a crude enzyme, more preferably, they should be concentrated in a conventional manner before use: For example, salting out method using ammonium sulfate, sedimentation method using acetone and alcohols, and concentration method using membranes such as plain filters and hollow fibers can be used to concentrate the cell-free cultures.

Intracellular enzymes can be extracted from the cells by conventional methods to obtain crude enzymes: For example, such crude enzymes can be extracted from the cells by disruption methods using ultrasonic, mechanical disruption method using glass beads and alumina, and other disruption methods using french-press. The extracts can be centrifugally separated or membrane filtered to obtain clear crude enzyme solutions.

Cell-free cultures, their concentrates, and extracts of cells can be immobilized by conventional methods: For example, binding method to ion-exchangers, covalent bonding and adsorption method to resins and membranes, and inclusion method using high molecular weight substances can be used for immobilization. Cells separated from microorganisms' cultures can be used as a crude enzyme, and the cells can be immobilized and used as an immobilized enzyme: For example, the cells are mixed with sodium alginate, and the mixture is dropped into a calcium chloride solution to form gelatinized granules which are then treated with polyethyleneimine and glutaraldehyde to form immobilized enzymes.

The crude enzymes thus obtained can be used intact and can be purified by conventional methods before use. For example, extracts from disrupted cells can be salted out using ammonium sulfate to obtain concentrated crude enzymes which are then dialyzed and purified by two or more techniques of anion exchange column chromatography using "SEPABEADS FP-DA13", anion exchange column chromatography using "DEAE-SEPHADEX A-50", gel filtration column chromatography using "ULTROGEL® AcA44", and hydrophobic chromatography using "BUTYL TOYOPEARL® 650M" to obtain purified enzymes with an electrophoretically single protein band.

The method for assaying the activity of the non-reducing saccharide-forming enzymes used in the present invention is as follows: Add one ml of an enzyme solution to 4 ml of 1.25 w/v % maltopentaose as a substrate dissolved in 50 mM phosphate buffer (pH 7.0), react the mixture at 40° C. for 60 min, heat the reaction mixture at 100° C. for 10 min to suspend the enzymatic reaction, precisely dilute the mixture with deionized water by 10-fold, and assay the reducing power of the dilution by the Somogyi-Nelson's method. As a control, an enzyme solution which had been heated at 100° C. for 10 min to inactivate the enzyme is assayed similarly as above. One unit activity of the enzyme is defined as the amount of enzyme which eliminates the reducing power of that of one micromole of maltopentaose per minute when assayed by the above method. In the case of non-reducing saccharide-forming enzymes from microorganisms of the genus Sulfolobus, the enzymes are reacted at 60° C. and pH 5.5, then inactivated by heating at 100° C. for 30 min.

The substrate concentration used in the present invention is not specifically restricted to: For example, the present enzymatic reaction proceeds even with a solution containing 0.1% or 50% maltooligosylsucrose as a substrate to produce maltooligosylturanose and maltooligosylpalatinose. The enzymatic reaction proceeds even with high-concentration solutions containing incompletely dissolved substrates. The reaction temperature used in the enzymatic reaction is in the range which does not inactivate the enzyme, i.e. up to a temperature of about 80° C., preferably, about 0°–70° C. Particularly, temperatures of about 30°–50° are preferably used for enzymes from microorganisms of the genus Arthrobacter to effectively produce maltooligosylturanose and maltooligosylpalatinose from maltooligosylsucrose. The reaction pH used in the enzymatic reaction is usually set to a pH of 5.5–9.0, preferably, a pH of about 6.0–8.5. The reaction time used in the enzymatic reaction is appropriately controlled depending on the enzymatic reaction rate and, usually, it is about 0.1–200 hours when used an about 10–1,000 units/g substrate, d.s.b., of an enzyme.

It was revealed that the reaction mixtures thus obtained usually contain maltooligosylturanose and maltooligosylpalatinose in a total amount of at least 10%, preferably, 15% or higher, more preferably, 60% or higher, d.s.b., with respect to the saccharide composition.

The reaction mixtures can be treated with conventional filtration and centrifugation methods to remove impurities, decolored with activated charcoals, desalted with ion exchangers in H—and OH—form, and concentrated into syrupy products and, if necessary, further dried into powdery products.

If necessary, these syrupy and powdery products can treated with higher-level purification methods: For example, these products can be subjected to fractionation such as column chromatography using ion exchangers, activated charcoals, or silica gels to facilitate the production of products rich in maltooligosylturanose and maltooligosylpalatinose. Maltooligosylsucrose separated by column chromatography can be arbitrarily reused as a substrate for non-reducing saccharide-forming enzymes to produce maltooligosylturanose and maltooligosylpalatinose.

The saccharide compositions comprising maltooligosylturanose and maltooligosylpalatinose thus obtained can be hydrolyzed by glucoamylase or β-amylase, and subjected to a saccharide-transferring reaction using cyclomaltodextrin glucanotransferase or glucosyltransferase after mixed with partial starch hydrolysates to control the sweetness and viscosity and, if necessary, further treated with yeasts to remove fermentable saccharides. The resulting mixtures can be treated with the above purification methods such as ion-exchange column chromatography to remove glucose and fructose and to collect fractions rich in maltooligosylturanose and maltooligosylpalatinose, followed by purifying and concentrating the fractions to obtain syrupy products. If necessary, the syrupy products can be further dried into powdery products.

As an example of ion-exchange column chromatography, column chromatography using strong-acid cation exchangers as disclosed in Japanese Patent Laid-Open Nos.23,799/83 and 72,598/83 can be advantageously used to remove concomitant saccharides and to collect fractions rich in maltooligosylturanose and maltooligosylpalatinose. In this case, fixed-bed, moving-bed, and quasi-moving-bed methods can be selectively used.

The present saccharide compositions comprising the maltooligosylturanose and maltooligosylpalatinose thus obtained could not be substantially crystallized and have a relatively-high water-solubility and a high quality and mild sweetness. Because these saccharides are hydrolyzed by intestinal hydrolytic enzymes into glucose and fructose moieties, they are readily digested and assimilated by animals including humans and used as an energy source when administered orally. These saccharides are not fermented by dental-caries inducing microorganisms and inhibit the formation of insoluble glucans from sucrose, so that they can be used as a sweetener with insubstantial dental-caries inducibility.

The saccharide compositions can be advantageously used as a sweetener, taste-improving agent, quality-improving agent, or stabilizer in products such as food products, tobaccos, cigarettes, feeds, pet foods, cosmetics, and pharmaceuticals.

The saccharide compositions can be used intact as a seasoning for sweetening. If necessary, the compositions can be used together with adequate amounts of one or more other sweeteners, for example, powdered syrup, glucose, fructose, maltose, sucrose, isomerized sugar, honey, maple sugar, sorbitol, maltitol, lactitol, dihydrochalcone, stevioside, α-glycosyl stevioside, rebaudioside, glycyrrhizin, L-aspartyl L-phenylalanine methyl ester, saccharin, glycine, and alanine, and/or a filler such as dextrins, starches, and lactose.

Because the present saccharide compositions have a taste that well harmonizes with other substances having sourness, acid, saltiness, bitterness, astringency, and deliciousness and have a satisfactory acid tolerance and heat tolerance, they can be freely used in food products in general as a sweetener, taste-improving agent, or quality-improving agent.

The present saccharide compositions can be used as a seasoning for soy sauce, powdered soy sauce, "miso", "funmatsumiso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "takuan-zuke-no-moto" (an instant mix for Japanese radish), "hakusai-zuke-no-moto" (an instant mix for Chinese cabbage), "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar.

The present saccharide compositions can be also used to sweeten and improve the taste and quality of "wagashi" (Japanese cakes) such as "senbei" (a rice cracker), "araremochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettarazuke" (a kind of whole fresh radish pickles), "senmai-zuke" (a kind of sliced fresh radish pickles) and "rakkyo-zuke" (pickled shallots); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish and shellfish; daily dishes such as "nimame" (cooked beans), potato salad and "konbu-maki" (a tangle roll); milk products; canned and bottled products such as those of meat, fish meat, fruit and vegetable; alcoholic beverages such as sake, synthetic sake, wine, and liquors; soft drinks such as coffee, tea, cocoa, juice, carbonated beverage, sour milk beverage, and beverage containing lactic acid bacteria; instant food products such as instant pudding mix, instant hot cake mix, and "sokuseki-shiruko" (an instant mix of adzuki-bean soup with rice cake) and instant soup mix; and beverages such as baby foods, foods for therapy, beverages supplemented with nutrition, peptide foods, and frozen foods; as well as for improving the tastes and qualities of the aforementioned food products.

The present saccharide compositions can be further used in feeds and pet foods for animals such as domestic animals, poultry, and fishes to improve their taste preferences. The saccharide compositions can be arbitrarily used as a sweetener, taste-improving agent, masking agent, or quality-improving agent in other products in a solid, paste, or liquid form such as tobaccos, cigarettes, dentifrices, lipsticks, rouges, chapped lips, internal medicines, tablets, trochees, cod liver oils in a drop form, cachous, oral refreshments, gargles, cosmetics, and pharmaceuticals.

Methods to incorporate the present saccharide compositions comprising maltooligosylturanose and maltooligosylpalatinose into the above products include conventional methods, for example, mixing, kneading, dissolving, melting, soaking, permeating, sprinkling, applying, coating, spraying, injecting, crystallizing, and solidifying. The present saccharide compositions are generally incorporated into those products in an amount of 0.1% or more, preferably, one % or more with respect to maltooligosylturanose and maltooligosylpalatinose.

The following experiments explain the present invention in more detail:

Experiment 1

Preparation of Maltotetraosylsucrose

Maltotetraosylsucrose was prepared according to the method disclosed in a section of Experiment in Japanese Patent Publication No. 58,905/82. Twenty-eight parts by weight of maltopentaose commercialized by Hayashibara Biochemical Laboratories, Inc., Okayama, Japan, and 12 parts by weight of commercially available sucrose were dissolved by heating in 60 parts by weight of water, and the solution was heated to 45° C. and adjusted to pH 6.5, then mixed with one unit/g sucrose, d.s.b., of levansucrase (EC 2.4.1.10) from a strain of the genus Bacillus before a 20 hours' enzymatic reaction. The reaction mixture was heated at 100° C. for 30 min to inactivate the remaining enzyme. The saccharide composition of the reaction mixture was analyzed by high-performance liquid chromatography (abbreviated as "HPLC" hereinafter) using the following: High-performance liquid chromatograph, "CCPM" commercialized by Tosoh Corporation, Tokyo, Japan; Column, "AQ-303 ODS (4.6 mmø×25 cm)", a column commercialized by YMC Co., Ltd., Kyoto, Japan; Eluent, purified and deionized water; Flow rate of eluent, 0.75 ml/min; Column temperature, 30° C.; Detector, "RI-8020", a differential refractometer commercialized by Tosoh Corporation, Tokyo, Japan.

Figure 1:
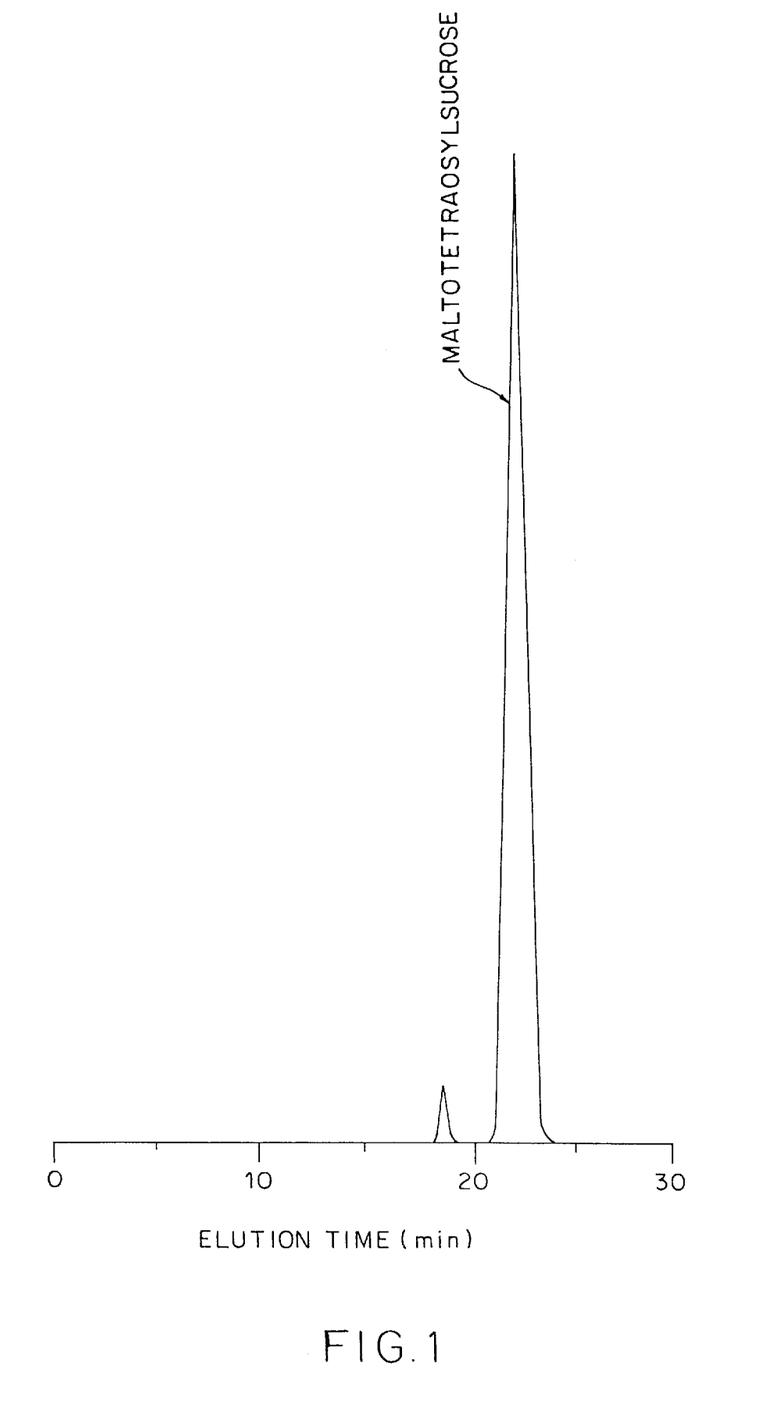
FIG. 1 is an HPLC chromatogram of a high purity maltotetraosylsucrose.

As a result, it was found that the reaction mixture contained 21% maltotetraosylsucrose. After adjusted to pH 12 by the addition of sodium hydroxide, reducing sugars in the reaction mixture were decomposed by heating at 100° C. for 30 min. The resulting solution was decolored with an activated charcoal, and deionized and purified with ion exchangers in H—and OH—form. The purified solution contained 62% maltotetraosylsucrose and 38% sucrose with respect to the saccharide composition. The solution was concentrated into an about 40% solution which was then column chromatographed using "AMBERLITE XT-1016 (Na-form)", a strong-acid cation exchanger commercialized by Japan Organo Co., Ltd, Tokyo, Japan, followed by collecting a fraction rich in maltotetraosylsucrose with a purity of about 98%. FIG.1 is an HPLC chromatogram of the fraction. The fraction was adjusted to pH 4.5 and heated to 55° C., then mixed with 20 units/g dry matter of "GLUCOZYME", glucoamylase commercialized by Nagase Biochemicals, Ltd., Kyoto, Japan, and subjected to an enzymatic reaction for 16 hours. The reaction mixture was heated at 100° C. for 15 min to inactivate the remaining enzyme. The HPLC analysis of the resulting product revealed that it had glucose and sucrose molecules in a molar ratio of 4:1 (=glucose:sucrose). Based on the data, the product was identified as maltotetraosylsucrose, i.e. 1-O-α-D-maltopentaosyl 2-O-β-D-fructofuranoside.

Experiment 2

Preparation of Enzyme

A liquid nutrient culture medium, consisting of 2.0 w/v % maltose, 0.5 w/v % peptone, 0.1 w/v % yeast extract, 0.2 w/v % disodium hydrogenphosphate, 0.05 w/v % magnesium sulfate, and water, was adjusted to pH 7.0, and about 100 ml aliquots of which were placed in 500-ml Erlenmeyer flasks, sterilized by autoclaving at 120° C. for 20 minutes, cooled, inoculated with a stock culture of Arthrobacter sp. Q36 (FERM BP-4316), and incubated at 28° C. for 24 hours under stirring conditions of 200 rpm. The resulting cultures were pooled for a seed culture.

About 20 L aliquots of a fresh preparation of the same nutrient culture medium used in the above culture were respectively placed in 30-L fermentors, sterilized by heating, cooled to 28° C., and inoculated with one v/v % of the seed culture, followed by the incubation at 28° C. and pH 6.5–8.0 for about 22 hours under agitation-aeration conditions.

Experiment 3

Purification of Enzyme

The culture prepared in Experiment 2 was centrifuged to obtain an about 0.6 kg wet cells of microorganisms. The cells were suspended in 10 mM phosphate buffer (pH 7.0), and about 1.9 L of the cell suspension was treated with "ULTRASONIC DISRUPTER MODEL US300", an ultrasonic disrupter commercialized by Nihonseiki Kaisha Ltd., Tokyo, Japan, to disrupt the cells. The resulting mixture was centrifuged at 15,000 g×30 min to obtain an about 1.8 L supernatant. Ammonium sulfate was added to and dissolved in the supernatant to give a saturation degree of 0.2, and the solution was allowed to stand at 4° C. overnight, and centrifuged to obtain a supernatant. To the supernatant was added ammonium sulfate and dissolved therein to give a saturation degree of 0.6, and the solution was allowed to stand at 4° C. overnight, then centrifuged to collect a precipitate.

The precipitate was dissolved in 10 mM phosphate buffer (pH 7.0), dialyzed against the same buffer for 24 hours, and centrifuged to remove insoluble substances. The supernatant thus obtained was subjected to anion exchange column chromatography using 380 ml of "SEPABEADS FP-DA13 GEL" commercialized by Mitsubishi Chemical Industries Ltd., Tokyo, Japan.

A non-reducing saccharide-forming enzyme was adsorbed on the "SEPABEADS FP-DA13 GEL" and eluted therefrom with a linear gradient buffer of a fresh preparation of the same buffer containing sodium chloride ranging from 0M to 0.5M. The enzyme eluted from the column was collected, dialyzed against a fresh preparation of the same buffer, and subjected to anion exchange column chromatography using 100 ml of "DEAE-SEPHADEX A-50" commercialized by Pharmacia LKB Biotechnology AB, Uppsala, Sweden. The enzyme was adsorbed on the gel and eluted therefrom with a linear gradient buffer of a fresh preparation of the same buffer containing sodium chloride ranging from 0M to 0.5M, and the eluted fractions with the enzyme activity were collected, pooled, and concentrated with "ULTRAFILTRATION MODUL PM-10", an ultrafilter commercialized by Amicon Div., W. R. Grace & Co., Beverly, Mass., USA, into a 6 ml solution.

The concentrated solution was subjected to gel filtration chromatography using a column packed with 630 ml of "ULTROGEL® AcA44", a gel commercialized by Sepracor Inc., MA, USA. The non-reducing saccharide-forming enzyme was eluted from the column with a fresh preparation of the same buffer containing one M sodium chloride without adsorbing on the gel.

The eluate was subjected to hydrophobic chromatography using a column packed with 7.8 ml of "BUTYL TOYOPEARL® 650M GEL" and eluted from the column with a linear gradient solution containing ammonium sulfate ranging from 1M to 0M to collect fractions with the enzyme activity. Thus an enzyme preparation with an electrophoretically single protein band was obtained. The specific activity of the enzyme was 203 units/mg protein.

Experiment 4

Action of Non-reducing Saccharide-forming Enzyme on Maltotetraosylsucrose

Figure 2:
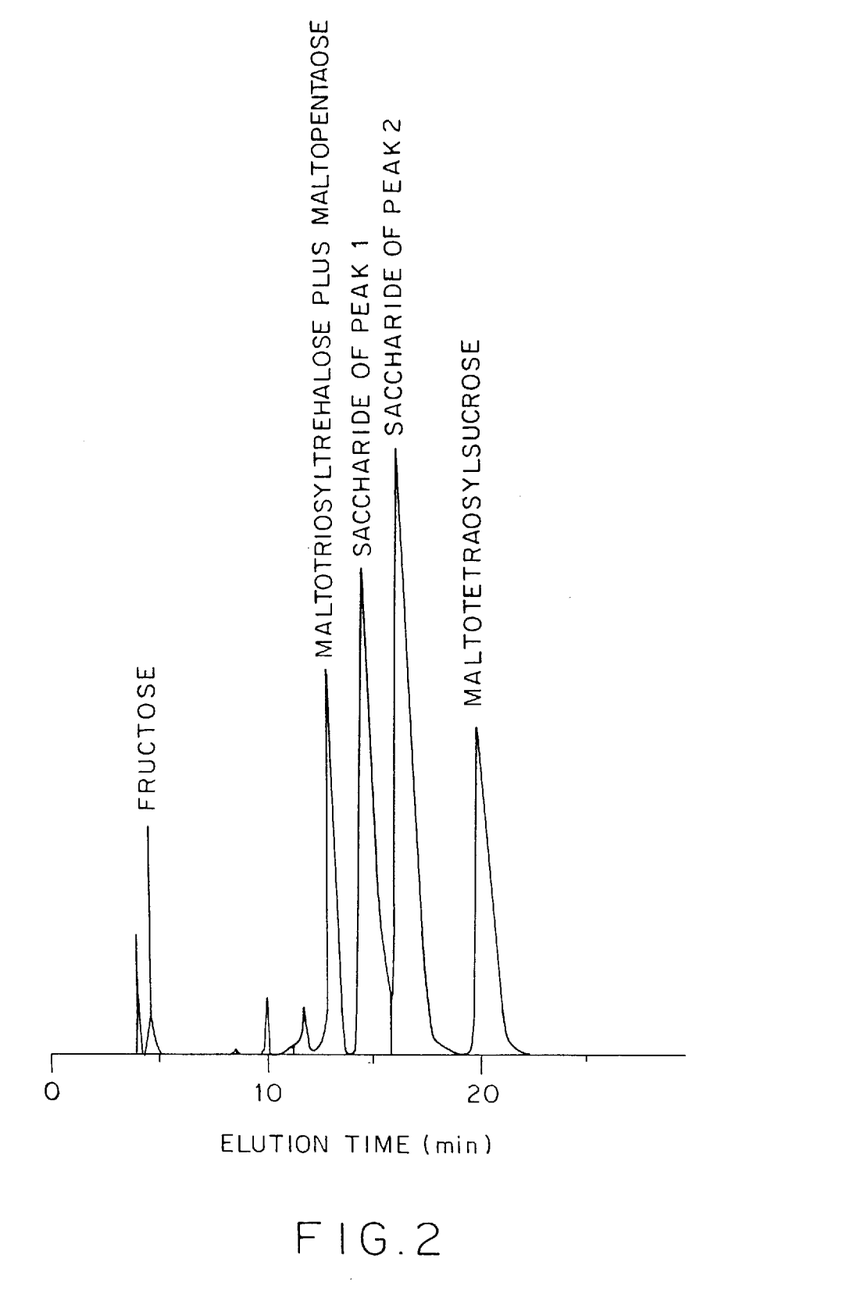
FIG. 2 is an HPLC chromatogram of a high purity maltotetraosylsucrose after hydrolyzed by a non-reducing saccharide-forming enzyme.

Forty parts by weight of maltotetraosylsucrose, obtained by the method in Experiment 1, was dissolved in 60 parts by weight of water. After heated to 40° C. and adjusted to pH 6.5, the solution was mixed with 100 units/g maltotetraosylsucrose, d.s.b., of a non-reducing saccharide-forming enzyme from Arthrobacter sp. Q36 (FERM BP-4316), obtained by the method in Experiment 3, subjected to an enzymatic reaction for 24 hours, and incubated at 100° C. for 30 min to inactivate the remaining enzyme. The reaction mixture was analyzed by HPLC in accordance with the method in Experiment 1. FIG.2 is an HPLC chromatogram of the reaction mixture. The mixture contained 27.9% of a saccharide of peak 1 and 35.9% of a saccharide of peak 2 with respect to the saccharide composition. The saccharides of peaks 1 and 2 were separatory collected using "YMC-Pack ODS R-355-15", a column, 5 cmØ×50 cm, for reverse-phase separatory fractionation commercialized by YMC Co., Ltd., Tokyo, Japan. While keeping a 2 w/v % solution of each saccharide at pH 4.5 and 40° C., 20 units/g dry matter of glucoamylase commercialized by Seikagaku-Kogyo Co., Ltd., Tokyo, Japan, was added to the solution and enzymatically reacted for 24 hours, followed by removing the enzyme using "MOL-CUT II", an ultrafiltration membrane commercialized by Japan Millipore Ltd., Tokyo, Japan, and subjecting the resulting solution to HPLC and thin-layer chromatography (abbreviated as "TLC" hereinafter) using "KIESELGEL 60", an aluminum plate, 20 cm×20 cm, commercialized by Merck & Co., Inc., N.J., USA, to analyze the saccharide composition. TLC was performed once at ambient temperature using a developing solvent system of 1-butanol, pyridine, and water (=6:4:1 by volume). The coloration was conducted by spraying 20 v/v % sulfuric acid in methanol to the plate and heating the plate at 110° C. for 10 min. From the saccharide of peak 1, glucose and turanose were formed in a molar ratio of 3.81:1, and this reveals that the saccharide of peak 1 is maltotetraosylturanose. From the saccharide of peak 2, glucose, palatinose, and trehalulose were formed in a molar ratio of 4.77:1:0.21. Considering the enzyme specificity of the non-reducing saccharide forming-enzyme to maltooligosaccharide and the structure of the saccharide of peak 1, it can be concluded that the saccharide of peak 2 contains a large amount of maltotetraosylpalatinose and a small amount of maltotetraosyltrehalulose.

Based on these data, it was found that the enzyme mainly forms maltotetraosylturanose and maltotetraosylpalatinose along with a small amount of maltotetraosyltrehalulose.

Experiment 5

Influence of the Amount of Enzyme Used to Form Maltotetraosylturanose, Maltotetraosylpalatinose, and Maltotetraosyltrehalulose A 40% maltotetraosylsucrose solution was mixed with 1, 4, 10, 20 or 100 units/g maltotetraosylsucrose, d.s.b., of a purified non-reducing saccharide-forming enzyme obtained by the method in Experiment 3, and enzymatically reacted at 40° C. and pH 6.5 for 24 hours. The remaining enzyme in the reaction mixture was removed by "MOL-CUT II", an ultrafiltration membrane commercialized by Japan Millipore Ltd., Tokyo, Japan, and the ultrafiltered solution was analyzed for saccharide composition by HPLC. The contents of the saccharides of peaks 1 and 2, formed with respective amounts of enzymes, were in Table 1.

TABLE 1

| Amount of enzyme | Substrate | Saccharide composition (%) Product | | | | |
|---|---|---|---|---|---|---|
| (unit/g) | A | B | C | D | E | F |
| 1 | 95.0 | 1.7 | 2.5 | 0.5 | 0.1 | 0.2 |
| 4 | 81.4 | 5.5 | 9.8 | 2.0 | 0.4 | 0.9 |
| 10 | 72.6 | 9.0 | 13.2 | 3.6 | 0.7 | 0.9 |
| 20 | 65.4 | 11.7 | 15.8 | 5.0 | 1.1 | 1.0 |
| 100 | 18.4 | 27.9 | 35.9 | 11.5 | 3.0 | 3.3 |

Note : In the table, the symbols "A", "B", "C", "D", "E" and "F" mean "maltotetraosylsucrose", "saccharide of peak 1", "saccharide of peak 2", "maltotriosyltrehalose and maltopentaose", "fructose", and "other saccharides", respectively.

As is evident from the result in Table 1, when used more than 4 units of the enzyme, the saccharide of peak 1 for maltotetraosylturanose and the saccharide of peak 2 for maltotetraosyltrehalulose were formed over 15% in total.

Experiment 6

Production of Maltotetraosylturanose, Maltotetraosylpalatinose, and Maltotetraosyltrehalulose from Maltotetraosylsucrose by Other Microorganisms' Non-reducing Saccharide-forming Enzymes In accordance with the methods in Experiments 2 and 3, purified non-reducing saccharide-forming enzymes from Arthrobacter sp. Q36 (FERM BP-4316) and Rhizobium sp. M-11 (FERM BP-4130) were prepared, and a partially purified non-reducing saccharide-forming enzyme from *Sulfolobus acidocaldarius* (ATCC 33909) was obtained by column chromatography using "DEAE-TOYOPEARL® 650". These enzymes were allowed to act on a 20% maltotetraosylsucrose solution for 96 hours under the conditions as shown in Table 2. The results were in Table 2.

TABLE 2

| Microorganism | Amount of enzyme (unit/g) | Reaction temperature (°C.) | Reaction pH | Yield* | Yield** |
|---|---|---|---|---|---|
| Arthrobacter sp. Q36 (FERM BP-4316) | 30 | 40 | 6.5 | 27.3 | 36.2 |
| Rhizobium sp. M-11 (FERM BP-4130) | 30 | 40 | 6.5 | 23.6 | 32.4 |
| *Sulfolobus acidocaldarius* (ATCC 33909) | 30 | 60 | 5.5 | 21.7 | 30.9 |

Note : In the table, the symbols "yield*" and "Yield**" mean "the yield (%) of maltotetraosylturanose" and "the yield (%) of maltotetraosylpalatinose plus maltotetraosyltrehalulose".

As is evident from the results in Table 2, it was found that the above enzymes readily form maltotetraosylturanose, maltotetraosylpalatinose, and maltotetraosyltrehalulose in a satisfactorily-high yield.

Experiment 7

Action of Non-reducing Saccharide-forming Enzyme on Maltooligosylsucrose

Maltotriose, maltotetraose, and maltohexaose as saccharide acceptors, all of which are commercialized by Hayashibara Biochemical Laboratories, Inc., Okayama, Japan, and sucrose were subjected to the action of levansucrase similarly as in Experiment 1 to produce maltosylsucrose, maltotriosylsucrose, and maltopentaosylsucrose, respectively. For saccharide analysis, saccharides consisting of 0–6 glucose moieties bound to sucrose such as the maltotetraosylsucrose obtained in Experiment 1, and commercially available sucrose and glucosylsucrose, i.e. erlose commercialized by Hayashibara Biochemical Laboratories, Inc, Okayama, Japan, were prepared as substrates. A non-reducing saccharide-forming enzyme from Arthrobacter sp. Q36 (FERM BP-4316), obtained by the method in Experiment 3, was allowed to act on the above saccharides similarly as in Experiment 4. Similarly as in Experiment 4, the reaction mixtures were analyzed by HPLC and determined for the yields of maltooligosylturanose, maltooligosylpalatinose, and maltooligosyltrehalulose which correspond to their respective substrates with a specific polymerization degree. The results were in Table 3.

TABLE 3

| Substrate | Yield* | Yield** |
|---|---|---|
| Sucrose | 0 | 0 |
| Glucosylsucrose | 0.6 | 0.9 |
| Maltosylsucrose | 3.7 | 4.9 |
| Maltotriosylsucrose | 29.7 | 34.6 |
| Maltotetraosylsucrose | 33.2 | 39.8 |
| Maltopentaosylsucrose | 35.2 | 41.8 |

Note : In the table, the symbols "Yield*" and "Yield**" mean "the yield (%) of maltooligosylturanose" and "the yield (%) of maltooligosylpalatinose plus maltooligosyltrehalulose".

As is evident from the results in Table 3, it was revealed that the non-reducing saccharide-forming enzyme specifically acts on maltooligosylsucrose as a substrate with a higher molecular weight than maltotriosylsucrose to intramolecularly convert sucrose moiety in the maltooligosylsucrose into maltooligosylturanose, maltooligosylpalatinose, and maltooligosyltrehalulose with easiness and in a relatively-high yield.

Experiment 8

Preparation of Maltooligosylturanose Maltooligosylpalatinose, and Maltooligosyltrehalulose From Maltooligosylsucrose Twenty-five parts by weight of α-cyclodextrin commercialized by Hayashibara Biochemical Laboratories, Inc., Okayama, Japan, and 25 parts by weight of commercially available sucrose were dissolved by heating in 50 parts by weight of water. After heated to 60° C. and adjusted to pH 6.0, the solution was inoculated with 5 units/g α-cyclodextrin of cyclomaltodextrin glucanotransferase from a strain of *Bacillus stearothermophilus* commercialized by Hayashibara Biochemical Laboratories, Inc., Okayama, Japan, and enzymatically reacted for 20 hours. The reaction mixture was heated at 100° C. for 30 min to inactivate the remaining enzyme. The mixture containing a variety of maltooligosylsucroses was heated to 40° C. and adjusted to pH 6.5, then mixed with 200 units/g dry matter of a non-reducing saccharide-forming enzyme from Arthrobacter sp. Q36 (FERM BP-4316) and enzymatically reacted for 24 hours. Thereafter, the reaction mixture was heated at 100° C. for 30 min to inactivate the remaining enzyme. The mixture contained a relatively large amount of maltooligosylturanose and maltooligosylpalatinose and a small amount of maltooligosyltrehalulose.

As is described above, the non-reducing saccharide-forming enzyme used in the present invention converts maltooligosaccharides into maltooligosyltrehalose and acts on maltooligosylsucrose to intramolecularly convert it into maltooligosylturanose and maltooligosylpalatinose to form a saccharide composition containing the converted saccharides.

Experiment 9

Acute Toxicity Test

By using dd-strain mice, 7-week old, a saccharide composition comprising maltotetraosylturanose and maltotetraosylpalatinose, obtained by the method in the later described Example A-4, was orally administered to the mice for acute toxicity test revealing that no mouse died up to a dose of 15 g/kg mouse, and a higher dose test was impossible. The data indicates that the saccharide composition is considerably low in toxicity. Another saccharide composition comprising maltooligosylturanose and maltooligosylpalatinose, obtained by the method in Example A-2, was orally administered to the mice for acute toxicity test. As a result, no mouse died up to a dose of 15 g/kg mouse revealing that the saccharide is also extremely low in toxicity.

The following Examples for Reference explain the preparation of the enzymes usable in the present invention, and Examples A and B explain the present process for producing saccharide compositions comprising maltooligosylturanose and maltooligosylpalatinose, and their uses, respectively:

Example for Reference 1

A seed culture of Arthrobacter sp. Q36 (FERM BP-4316) was inoculated into a liquid nutrient culture medium consisting of 4.0 w/v % glucose, 0.5 w/v % polypeptone, 0.1 w/v % yeast extract, 0.1 w/v % dipotassium hydrogen phosphate, 0.06 w/v % sodium dihydrogen phosphate, 0.05 w/v % magnesium sulfate heptahydrate, and water, and cultured in a fermentor for about 60 hours under aeration-agitation conditions in accordance with the method in Experiment 2 except for culturing at 27° C. An about 18 L of the culture was treated with "MINI-LABO", a superpressure cell disrupter commercialized by Dainippon Pharmaceutical Co., Ltd., Tokyo, Japan, to disrupt the cells. The cell suspension was centrifuged to obtain a supernatant which was then purified in accordance with the method in Experiment 3 to obtain an about 300 ml of a partially purified solution containing about 30 units/ml of a non-reducing saccharide-forming enzyme.

Example for Reference 2

A seed culture of Rhizobium sp. M-11 (FERM BP-4130) was inoculated into a liquid nutrient culture medium consisting of 2.0 w/v % glucose, 0.5 w/v % peptone, 0.1 w/v % yeast extract, 0.1 w/v % dipotassium hydrogen phosphate, 0.1 w/v % potassium dihydrogen phosphate, and water, and cultured in a fermentor for about 24 hours under aeration-agitation conditions in accordance with the method in Experiment 2 except for culturing at 30° C. An about 18 L of the culture was centrifuged to obtain about 0.4 kg wet cells of microorganisms which were then suspended in 4 L of 10 mM phosphate buffer and treated with an ultrasonic disintegrator to disrupt the cells. The cell suspension was centrifuged to obtain a supernatant. Thereafter, an about 100 ml of a partially purified enzyme solution, containing about 15 units/ml of a non-reducing saccharide-forming enzyme, was obtained in accordance with the method in Experiment 3.

Example for Reference 3

One hundred ml aliquots of a liquid nutrient culture medium, consisting of 0.1 w/v % peptone, 0.1 w/v % yeast extract, 0.2 w/v % ammonium sulfate, 0.05 w/v % potassium dihydrogen phosphate, 0.02 w/v % magnesium sulfate heptahydrate, 0.02 w/v % potassium chloride, and water, were distributed into 500-ml Erlenmeyer flasks, sterilized by autoclaving at 120° C. for 20 min, cooled, and adjusted to pH 3.0 by the addition of sulfuric acid. The resulting culture medium was inoculated with a stock culture of *Sulfolobus acidocaldarius* (ATCC 33909) and cultured at 75° C. for 24 hours under shaking conditions of 130 rpm. The culture thus obtained was used as a first seed culture.

About 20 L aliquots of a fresh preparation of the same liquid nutrient culture medium used in the above were placed in 30-L fermentors, sterilized by heating, cooled, adjusted to pH 3.0, and heated to 75° C. Thereafter, one v/v % of the first seed culture was inoculated into each fermentor and cultured at 75° C. for about 48 hours under aeration-agitation conditions. The resulting culture was used as a second seed culture. About 250 L aliquots of a fresh preparation of the same liquid nutrient culture medium used in the above were placed in 300-L fermentors, sterilized by heating, cooled, adjusted to pH 3.0, and heated to 75° C. Thereafter, one v/v % of the second seed culture was inoculated into each fermentor and incubated at 75° C. for about 42 hours under aeration-agitation conditions. About 170 L of the culture was treated with an SF membrane and centrifuged to obtain 258 g wet cells. The cells were mixed with and suspended in 300 ml of 10 mM phosphate buffer (pH 7.0), then treated with an ultrasonic disintegrator to disrupt the cells. The resulting cell suspension was centrifuged to obtain a supernatant which was then subjected to ion-exchange chromatography using "DEAE-TOYOPEARL®" and hydrophobic column chromatography using "BUTYL-TOYOPEARL® 650" to obtain an about 50 ml of a partially purified enzyme solution containing about 10 units/ml of a non-reducing saccharide-forming enzyme.

Example A-1

Two and half parts by weight of sucrose and 3.5 parts by weight of "PENTRUP®", maltooligosaccharide commercialized by Hayashibara Co., Ltd., Okayama, Japan, were dissolved by heating in 4 parts by weight of water, and the solution was adjusted to pH 6.5, heated to 45° C., inoculated with one unit/g sucrose of leveansucrase (EC 2.4.1.10) from a strain of the genus Bacillus, and enzymatically reacted for 20 hours. The reaction mixture was then heated to inactivate the remaining enzyme, mixed with 50 units/g dry matter of a non-reducing saccharide-forming enzyme from a strain of the genus Arthrobacter obtained by the method in Example for Reference 1, incubated at 40° C. for 40 hours for enzymatic reaction, and heated to inactivate the remaining enzyme. The reaction mixture thus obtained was in a conventional manner decolored with an activated charcoal, deionized, purified with ion exchangers in H— and OH—form, and concentrated into a syrup containing about 75% maltooligosylturanose and maltooligosylpalatinose in a yield of about 93%. Because the syrup with non-crystallinity contains about 20% maltooligosylturanose and maltooligosylpalatinose and has a satisfactory sweetness, adequate viscosity, and moisture-retaining ability, it can be arbitrarily used in food products, cosmetics, and pharmaceuticals. The reducing saccharides in the product such as maltooligosylturanose and maltooligosylpalatinose can be arbitrarily hydrogenated into their corresponding non-reducing sugar alcohols before use.

Example A-2

Twenty-five parts by weight of sucrose and 25 parts by weight of α-cyclomaltodextrin commercialized by Hayashibara Biochemical Laboratories, Inc., Okayama, Japan, were dissolved by heating in 50 parts by weight of water. The solution was heated to 60° C., adjusted to pH 5.5, mixed with 5 units/g α-cyclomaltodextrin, d.s.b., of cyclomaltodextrin glucanotransferase from a strain of the species *Bacillus stearothermophilus* commercialized by Hayashibara Biochemical Laboratories, Inc., Okayama, Japan, and enzymatically reacted for 20 hours. The reaction mixture was heated to inactivate the remaining enzyme, mixed with 100 units/g dry matter of a non-reducing saccharide-forming enzyme from a strain of the genus Arthrobacter obtained by the method in Example for Reference 1, and enzymatically reacted at 40° C. for 20 hours. Thereafter, the resulting mixture was heated to inactivate the remaining enzyme.

The mixture thus obtained was in a conventional manner decolored with an activated charcoal, desalted and purified with ion exchangers in H— and OH—form, concentrated, dried in vacuo, and pulverized to obtain a saccharide powder containing maltooligosylturanose and maltooligosylpalatinose in a yield of about 90%. The powder with non-crystallinity contained about 20% maltooligosylturanose and maltooligosylpalatinose. Similarly as the product in Example A-1, the powder has a satisfactory sweetness, adequate viscosity, and moisture-retaining ability, and because of this it can be arbitrarily used in a variety of compositions.

Example A-3

To 5 parts by weight of "COUPLING SUGAR®", a glycosylsucrose with a moisture content of about 25% commercialized by Hayashibara Co., Ltd., Okayama, Japan, was added 5 parts by weight of water, and the solution was heated to 45° C., adjusted to pH 6.5, mixed with 50 units/g dry matter of a non-reducing saccharide-forming enzyme from a strain of the genus Rhizobium obtained by the method in Example for Reference 2, enzymatically reacted for 30 hours, and heated to inactivate the remaining enzyme. The reaction mixture was in a conventional manner decolored with an activated charcoal, desalted and purified with ion exchangers in H— and OH—form, and concentrated to obtain a syrup containing about 75% maltooligosylturanose and maltooligosylpalatinose in a yield of about 93%. The syrup with non-crystallinity contained about 15% maltooligosylturanose and maltooligosylpalatinose. Because the syrup has a satisfactory sweetness, adequate viscosity, and moisture-retaining ability, it can be arbitrarily used in food products, cosmetics, and pharmaceuticals.

Example A-4

Two and half parts by weight of sucrose and 2.5 parts by weight of maltopentaose commercialized by Hayashibara Biochemical Laboratories, Inc., Okayama, Japan, were dissolved by heating in 5 parts by weight of water, and the solution was adjusted to pH 6.5 and 45° C., admixed with one unit/g sucrose of levansucrase from a strain of the genus Bacillus, enzymatically reacted for 20 hours, and heated to inactivate the remaining enzyme. The reaction mixture was in a conventional manner decolored with an activated charcoal, desalted and purified with ion exchangers in H—and OH—form, and fractionated using an "ODS" column for fractionation to obtain a high-purity maltotetraosylsucrose solution. To the solution was added 50 units/g dry matter of a thermostable non-reducing saccharide-forming enzyme from a strain of the genus Sulfolobus obtained by the method in Example for Reference 3, enzymatically reacted at 65° C. for 20 hours, and heated to inactivate the remaining enzyme. The reaction mixture was in a usual manner decolored with an activated charcoal, desalted and purified with ion exchangers in H—and OH—form, concentrated, and spray dried to obtain a powder containing maltooligosylturanose and maltooligosylpalatinose in a yield of about 85%. The powder with non-crystallinity contained about 55% maltotetraosylturanose and maltotetraosylpalatinose and about 18% maltotetraosylsucrose. Because the powder has a satisfactory sweetness, it can be arbitrarily used in food products, cosmetics, and pharmaceuticals.

Example B-1

Sweetener

One part by weight of a saccharide powder containing maltotetraosylturanose and maltotetraosylpalatinose, obtained by the method in Example A-4, and 0.05 part by weight of "αG SWEET", α-glycosyl stevioside commercialized by Toyo Sugar Refining Co., Ltd., Tokyo, Japan, were mixed to homogeneity, and the mixture was subjected to a granulator to obtain a granular sweetener. The product has a satisfactory sweetness, a two-fold higher sweetening power of sucrose, and an about half calorific value of sucrose with respect to the sweetening power. The product can be arbitrarily used as a low-caloric sweetener to sweeten low-caloric foods for overweight persons and diabetics who are restricted to caloric intake. Because the product less forms acids and insoluble glucans when assimilated by dental caries-inducing microorganisms, it can be arbitrarily used to sweeten food products which prevent dental caries.

Example B-2

Hard Candy

One hundred parts by weight of a 55% maltooligosylsucrose solution was mixed while heating with 30 parts by weight of a syrup containing maltooligosylturanose and maltooligosylpalatinose obtained by the method in Example A-1, and the solution was concentrated by heating under a reduced pressure up to give a moisture content of below 2%. The concentrate was admixed with one part by weight of citric acid and adequate amounts of a lemon flavor and a coloring agent, and the mixture was shaped in a conventional manner into a desired product, i.e. a high-quality hard candy with a satisfactory biting-property and taste. The crystallization of maltooligosylsucrose in the product is well prevented.

Example B-3

Strawberry Jam

One hundred and fifty parts by weight of fresh strawberry, 60 parts by weight of maltooligosylsucrose, 20 parts by weight of maltose, 40 parts by weight of a syrup containing maltooligosylturanose and maltooligosylpalatinose obtained by the method in Example A-1, 5 parts by weight of pectin, and one part by weight of citric acid were boiled in a plain pan and bottled to obtain a desired product, i.e. a jam with a satisfactory flavor and color.

Example B-4

Lactic Acid Beverage

Ten parts by weight of skim milk was sterilized by heating at 80° C. for 20 min, cooled to 40° C., inoculated with 0.3 part by weight of a starter, and fermented at about 37° C. for 10 hours. The fermented mixture was homogenized, admixed with 4 parts by weight of a saccharide powder containing maltooligosylturanose and maltooligosylpalatinose obtained by the method in Example A-2, one part by weight of maltooligosylsucrose, and 2 parts by weight of an isomerized syrup, and sterilized by heating at 70° C. The resulting mixture was cooled and bottled to obtain a desired product, i.e. a high-quality lactic acid beverage with a satisfactory flavor and sweetness well harmonized with acid.

Example B-5

Sweetened Milk

In 100 parts by weight of fresh milk were dissolved one part by weight of maltooligosylsucrose and 3 parts by weight of a syrup, containing maltooligosylturanose and maltooligosylpalatinose, obtained by the method in Example A-3. The solution was sterilized by heating with a plate heater and concentrated into an about 70% solution which was then sterilely bottled into a desired product. Because the product has a mild sweetness and a satisfactory flavor, it can be arbitrarily used to season foods for babies and infants, fruits, coffees, cocoas, and teas.

Example B-6

Chewing Gum

Three parts by weight of a gum base was melted by heating until softened, admixed with 6 parts by weight of maltooligosylsucrose, one part by weight of a saccharide powder containing maltotetraosylturanose and maltotetraosylpalatinose obtained by the method in Example A-4, and further mixed with adequate amounts of a flavor and a coloring agent. The resulting mixture was kneaded by a roll and shaped into a desired product, i.e. a chewing gum with a satisfactory flavor and texture.

Example B-7

Custard Cream

One hundred parts by weight of corn starch, 100 parts by weight of a syrup containing maltooligosylturanose and maltooligosylpalatinose obtained by the method in Example A-3, 80 parts by weight of maltose, 20 parts by weight of maltooligosylsucrose, and one part by weight of salt were mixed sufficiently. To the mixture was added 280 parts by weight of fresh eggs, and the mixture was stirred, gradually mixed with 1,000 parts by weight of a boiling milk, and heated while stirring, and the heating was terminated when the whole contents were completely gelatinized to show a semitransparency. The gelatinized mixture was cooled, admixed with an adequate amount of a vanilla flavor, weighed, injected, and packed to obtain a desired product with a smooth surface and a mild and tastable sweetness.

Example B-8

Uiro-no-moto (Premix for Sweet Rice Jelly)

Ninety parts by weight of rice powder, 20 parts by weight of corn starch, 120 parts by weight of a saccharide powder containing maltotetraosylturanose and maltotetraosylpalatinose obtained by the method in Example A-4, and 4 parts by weight of pullulan were mixed to homogeneity to obtain an uiro-no-moto. The product was kneaded with adequate amounts of matcha (powdered tea) and water, and the mixture was placed in a container and steamed up over 60 min to obtain a matcha uiro. The product has a satisfactory gloss and a desirable biting property and flavor and has a satisfactorily-long shelf life because the retrogradation of starch is well prevented.

Example B-9

Solid Preparation for Intubation Feeding

A composition, consisting of 500 parts by weight of a saccharide powder containing maltotetraosylturanose and maltotetraosylpalatinose obtained by the method in Example A-4, 270 parts by weight of powdered yolk, 209 parts by weight of skim milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 part by weight of vitamin E acetate, and 0.04 part by weight of nicotinic acid amide, was prepared. Twenty-five g aliquots of the composition were injected into moisture-proof small laminated bags which were then heat sealed. One bag of the product is dissolved in about 150–300 ml water to obtain a fluid food and administered orally to humans or administered to the nasal cavity, stomach, or intestines by intubation feeding, etc.

Example B-10

Ointment for Treating Skin Trauma

Five hundred parts by weight of a saccharide powder containing maltotetraosylturanose and maltotetraosylpalatinose obtained by the method in Example A-4 was admixed with 3 parts by weight of iodine dissolved in 50 parts by weight of methanol, further mixed with 200 parts by weight of a 10% aqueous pullulan solution to obtain an ointment for treating trauma with a satisfactory spreadability and adhesiveness. The ointment shortens the healing period and completely cures the wounded parts.

As is evident from the above, saccharide compositions comprising maltooligosylturanose and maltooligosylpalatinose are readily produced, separated, and purified in a relatively high yield from maltooligosylsucrose by allowing non-reducing saccharide-forming enzymes to act on aqueous solutions containing maltooligosylsucrose. These saccharides are reducing oligosaccharides, which consist of glucose and fructose moieties and have a mild and high-quality sweetness, can be used orally and parenterally, and readily metabolized by living bodies without fear of toxicity and of causing side effects.

The saccharide compositions comprising maltooligosyl-turanose and maltooligosylpalatinose according to the present invention are non-crystalline saccharides and readily handleable regardless of their form of a liquid or a powder. The compositions have a desirable osmosis-controlling ability, filler-imparting ability, gloss-imparting ability, moisture-retaining ability, viscosity-imparting ability, crystallization-preventing ability for other saccharides, and insubstantial fermentability. Because of these satisfactorily properties, the compositions can be advantageously used in compositions as a sweetener, taste-improving agent, quality-improving agent, and stabilizer.

Therefore, the establishment of the saccharide compositions comprising maltooligosylturanose and maltooligosylpalatinose, their preparations, and uses thereof made by the present invention would greatly contributes to this field.

While there has been described what is at present considered to be the preferred embodiments of the present invention, it will be understood the various modifications may be made therein, and it is intended to cover in the appended claims all such modifications as fall within the true spirits and scope of the invention.

We claim:

1. A saccharide composition comprising maltooligosyl derivatives of turanose and palatinose.

2. The saccharide composition of claim 1, which additionally contains maltooligosyltrehalulose.

3. The saccharide composition of claim 1, which is obtainable by allowing a non-reducing saccharide-forming enzyme to act on a solution containing maltooligosylsucrose.

4. The saccharide composition of claim 3, wherein said enzyme is derivable from a microorganism.

5. The saccharide composition of claim 4, wherein said microorganism is one selected from the group consisting of those of the genera Rhizobium, Arthrobacter, and Sulfolobus.

6. The saccharide composition of claim 1, which contains at least 15 w/w % of said maltooligosyl derivatives of turanose and palatinose, on a dry solid basis.

7. A process for producing a saccharide composition comprising maltooligosyl derivatives of turanose and palatinose, which comprises allowing a non-reducing saccharide-forming enzyme to act on a solution containing maltooligosylsucrose to produce said maltooligosyl derivatives of turanose and palatinose, and recovering the produced maltooligosyl derivatives of turanose and palatinose.

8. The process of claim 7, wherein said enzyme is allowed to act on the solution in an amount of at least 4 units/g dry matter.

9. A food product prepared by incorporating the saccharide composition of claim 1 into a food material.

10. The food product of claim 9, which contains at least 0.1% of maltooligosyl derivatives of turanose and palatinose, on a dry solid basis, contained in the saccharide composition.

11. The food product of claim 9, wherein said saccharide composition is produced by allowing a non-reducing saccharide-forming enzyme to act on a solution containing maltooligosylsucrose.

12. A cosmetic composition prepared by incorporating the saccharide composition of claim 1 into a cosmetically-acceptable carrier.

13. The cosmetic composition of claim 12, which contains at least 0.1% of maltooligosyl derivatives of turanose and palatinose, on a dry solid basis, contained in the saccharide composition.

14. The cosmetic composition of claim 12, wherein said saccharide composition is produced by allowing a non-reducing saccharide-forming enzyme to act on a solution containing maltooligosylsucrose.

15. A pharmaceutical composition prepared by incorporating the saccharide composition of claim 1 into a pharmaceutically-acceptable carrier.

16. The pharmaceutical composition of claim 15, which contains at least 0.1% of maltooligosyl derivatives of turanose and palatinose, on a dry solid basis, contained in the saccharide composition.

17. The pharmaceutical composition of claim 15, wherein said saccharide composition is produced by allowing a non-reducing saccharide-forming enzyme to act on a solution containing maltooligosylsucrose.

* * * * *